United States Patent
Mako, Jr. et al.

(10) Patent No.: US 10,093,865 B2
(45) Date of Patent: *Oct. 9, 2018

(54) SYSTEM AND METHOD FOR PRODUCING CHEMICALS AT HIGH TEMPERATURE

(71) Applicants: Frederick M. Mako, Jr., Fairfax Station, VA (US); Edward Jeffrey Cruz, Sterling, VA (US); Frederick M. Mako, Fairfax Station, VA (US)

(72) Inventors: Frederick M. Mako, Jr., Fairfax Station, VA (US); Edward Jeffrey Cruz, Sterling, VA (US); Frederick M. Mako, Fairfax Station, VA (US)

(73) Assignee: Frederick M. Mako, Jr., Fairfax Station, VA (US)

( * ) Notice: Subject to any disclaimer, the term of this patent is extended or adjusted under 35 U.S.C. 154(b) by 3 days.

This patent is subject to a terminal disclaimer.

(21) Appl. No.: 15/415,528

(22) Filed: Jan. 25, 2017

(65) Prior Publication Data

US 2017/0130139 A1  May 11, 2017

Related U.S. Application Data

(62) Division of application No. 14/656,253, filed on Mar. 12, 2015.

(Continued)

(51) Int. Cl.
*C10G 9/20* (2006.01)
*C10G 9/16* (2006.01)

(Continued)

(52) U.S. Cl.
CPC ............... *C10G 9/203* (2013.01); *C07C 4/04* (2013.01); *C10G 9/16* (2013.01); *C10L 1/06* (2013.01);

(Continued)

(58) Field of Classification Search
CPC .... C07C 4/00; C07C 4/02; C07C 4/04; C10G 9/00; C10G 9/14; C10G 9/16; C10G 9/20; C10G 9/203; C10G 2400/00; C10G 2400/02; C10L 1/00; C10L 1/04; C10L 1/06; C10L 2200/04–2200/0423; C10L 2270/00–2270/023; F16L 13/00; F16L 13/007; F16L 13/08; F16L 41/00;

(Continued)

(56) References Cited

U.S. PATENT DOCUMENTS 4,299,538 A * 11/1981 Ferris .................... B64C 27/33
    416/134 A
4,316,936 A *  2/1982 Hing ..................... C04B 37/025
    428/325

(Continued)

*Primary Examiner* — Natasha E Young
(74) *Attorney, Agent, or Firm* — Ansel M. Schwartz

(57) ABSTRACT

A system for producing chemicals, such as, ethylene or gasoline, at high temperature (above 1100 degrees C.) having a feedstock source. The system includes a chemical conversion portion connected with the feedstock source to receive feedstock and convert the feedstock to ethylene or gasoline. The conversion portion includes a coil array and a furnace that heats the feedstock to temperatures in excess of 1100° C. or 1200° C. or even 1250° C. or even 1300° C. or even 1400° C. A method for producing chemicals, such as ethylene or gasoline, at high temperature.

14 Claims, 13 Drawing Sheets

Assembled 3D Joint

Related U.S. Application Data

(60) Provisional application No. 61/952,492, filed on Mar. 13, 2014, provisional application No. 61/971,941, filed on Mar. 28, 2014, provisional application No. 61/972,582, filed on Mar. 31, 2014, provisional application No. 61/972,630, filed on Mar. 31, 2014, provisional application No. 61/973,027, filed on Mar. 31, 2014, provisional application No. 61/973,085, filed on Mar. 31, 2014.

(51) Int. Cl.
*C10L 1/06* (2006.01)
*C07C 4/04* (2006.01)
*F16L 13/007* (2006.01)
*F16L 41/08* (2006.01)
*F16L 49/02* (2006.01)
*B01J 19/00* (2006.01)
*B01J 19/24* (2006.01)
*F16L 13/08* (2006.01)

(52) U.S. Cl.
CPC .............. *F16L 13/007* (2013.01); *F16L 13/08* (2013.01); *F16L 41/084* (2013.01); *F16L 49/02* (2013.01); *C10G 2400/02* (2013.01); *C10L 2200/0423* (2013.01); *C10L 2270/023* (2013.01)

(58) Field of Classification Search
CPC .......... F16L 41/08–41/084; F16L 49/00; F16L 49/02; B01J 19/00; B01J 19/24; B01J 2219/24
See application file for complete search history.

(56) References Cited

U.S. PATENT DOCUMENTS

| | | | |
|---|---|---|---|
| 8,998,268 B2 * | 4/2015 | Banach | F16L 13/00 156/89.11 |
| 2011/0257455 A1 * | 10/2011 | Spicer | B01J 19/0073 585/648 |
| 2015/0260322 A1 * | 9/2015 | Mako, Jr. | B32B 1/08 428/586 |

* cited by examiner

Tapered 3D Joint

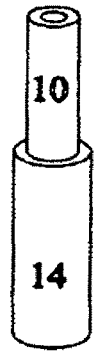
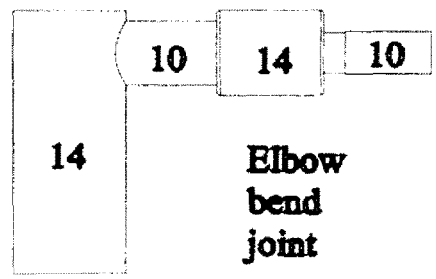
Large diameter to small diameter lap joint
Elbow bend joint
FIG. 3a  FIG. 3b
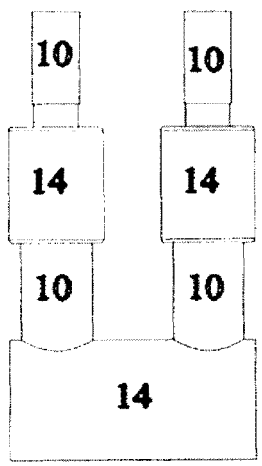
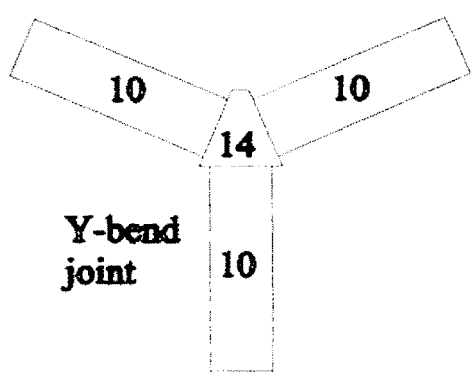
U-bend joint
Y-bend joint
FIG. 3c  FIG. 3d

SYSTEM AND METHOD FOR PRODUCING CHEMICALS AT HIGH TEMPERATURE

CROSS-REFERENCE TO RELATED APPLICATIONS

This is a divisional of U.S. patent application Ser. No. 14/656,253 filed Mar. 12, 2015, which is a nonprovisional application of U.S. provisional application Ser. Nos. 61/952,492 filed Mar. 13, 2014; 61/971,941 filed Mar. 28, 2014; 61/972,582 filed Mar. 31, 2014; 61/972,630 filed Mar. 31, 2014; and 61/973,027 filed Mar. 31, 2014; 61/973,085 filed Mar. 31, 2014, all of which are incorporated by reference herein.

FIELD OF THE INVENTION

The present invention is related to joining of ceramic and metal bodies for applications involving temperatures over 1100° C., such as ethylene or gasoline production. (As used herein, references to the "present invention" or "invention" relate to exemplary embodiments and not necessarily to every embodiment encompassed by the appended claims.) More specifically, the present invention is related to joining of ceramic and metal bodies for applications involving temperatures over 1100° C., such as ethylene or gasoline production, with the use of coils made of silicon carbide joined to a superalloy with a tungsten coupling.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Ethylene is used as the building block for the production of polyethylene, glycol polyester, and styrene monomer. Global production of ethylene from olefin plants has reached over 150 million metric-tons in 2012, according to Gulf Petrochemicals and Chemicals Association, making ethylene one of the largest produced chemical commodities, by volume, in existence today.

Production of ethylene is achieved by cracking a gaseous or liquid hydrocarbon feedstock, such as ethane, propane, naphtha, or gas oil in the presence of steam inside the coils of a pyrolysis furnace. Hydrocarbon cracking is accomplished at low pressures (up to a few atmospheres) and elevated temperatures in the range of 750-1150° C. feedstock is passed at high velocities through heated coils which are made from superalloys primarily comprised of iron, nickel and chromium. The hydrocarbon cracking time, or residence time, within the coils is extremely short, generally less than a fraction of a second.

These pyrolysis furnace coils are subjected to some of the most severe operating conditions in the petrochemical industry, experiencing extreme thermal cycling, coking, carburization, oxidation and creep during service, resulting in reduced service life and frequent premature pipe failures. This family of iron, nickel and chromium superalloys may well have reached their ultimate operating limits as the past few decades have seen a trend of increasing furnace temperature in efforts to increase yield and efficiency from the endothermic cracking process. Furthermore, this metal superalloy combination in general has always been hindered by temperature limits and the frequent maintenance required for coke removal. The main objective of this invention is to provide an alternative path to achieve coils operating at higher temperature with reduced coking, thus increasing the production capabilities of ethylene furnaces. This alternative path described here will be through the use primarily of silicon carbide.

BRIEF SUMMARY OF THE INVENTION

The present invention pertains to a system for producing chemicals at high temperature (above 1100 degrees C.), such as, ethylene or gasoline. The system comprises a feedstock source. The system comprises a chemical conversion portion connected with the feedstock source to receive feedstock and convert the feedstock to ethylene or gasoline. The conversion portion includes a coil array and a furnace that heats the feedstock to temperatures in excess of 1100° C. or 1200° C. or even 1250° C. or even 1300° C. or even 1300° C., The coil array has a plurality of coils. Each coil has a right top portion made of super alloy that connects with the source to receive feedstock, a right oxidation protected tungsten coupling that is attached outside the furnace to the right top portion and forms a helium gas tight seal with the right top portion, a right bottom portion made of silicon carbide that is attached to the right oxidation protected tungsten coupling and forms a helium gas tight seal with the right oxidation protected tungsten coupling, a base made of silicon carbide that is attached to the right bottom portion and forms a helium gas tight seal with the right bottom portion, a left bottom portion made of silicon carbide that is attached to the base and forms a helium gas tight seal with the base, a left oxidation protected tungsten coupling that is attached to the left bottom portion and forms a helium gas tight seal with the left bottom portion, and a left top portion made of super alloy that is attached outside the furnace to the left oxidation protected tungsten coupling and forms a helium gas tight seal with the left oxidation protected tungsten coupling. The right top portion and the right oxidation protected tungsten coupling and the right bottom portion and the base and the left bottom portion and the left oxidation protected tungsten coupling and the left top portion being hollow and defining a channel through which feedstock flows and is heated by the furnace to produce ethylene or gasoline from the feedstock. The furnace heats the left bottom portion and the base and the right bottom portion to temperatures in excess of 1100° C. The system comprises a reservoir connected with the left top portion of each coil to receive ethylene or gasoline from the left top portion of each coil.

The present invention, pertains to a method for producing ethylene or gasoline. The method comprises the steps of flowing feedstock from a feedstock source to a chemical conversion portion connected with the feedstock source to receive feedstock and convert the feedstock to ethylene or gasoline. The conversion portion includes a coil array and a furnace that heats the feedstock to temperatures in excess of 1100° C. or 1200° C. or even 1250° C. or even 1300° C. or even 1400° C. The coil array has a plurality of coils. Each coil has a right top portion made of super alloy that connects with the source to receive feedstock, a right oxidation protected tungsten coupling that is attached outside the furnace to the right top portion and forms a helium gas tight seal with the right top portion, a right bottom portion made of silicon carbide that is attached to the right oxidation protected tungsten coupling and forms a helium gas tight seal with the right oxidation protected tungsten coupling, a base made of silicon carbide that is attached to the right bottom portion and forms a helium gas tight seal with the right bottom portion, a left bottom portion made of silicon carbide that is attached to the base and forms a helium gas tight seal with the base, a left oxidation protected tungsten coupling that is attached to the left bottom portion and forms a helium gas tight seal with the left bottom portion, and a left top portion made of super alloy that is attached outside the furnace to the left oxidation protected tungsten coupling and forms a helium gas tight seal with the left oxidation protected tungsten coupling. The right top portion and the right oxidation protected tungsten coupling and the right bottom portion and the base and the left bottom portion and the left oxidation protected tungsten coupling and the left top portion being hollow and defining a channel through which feedstock flows and is heated by the furnace to produce ethylene or gasoline from the feedstock. The furnace heats the left bottom portion and the base and the right bottom portion to temperatures in excess of 1100° C. There is the step of receiving ethylene or gasoline at a reservoir from the left top portion of each coil.

The present invention pertains to a method for forming an assembly. The method comprises the steps of placing a first tube of silicon carbide or mullite adjacent a second tube of silicon carbide or mullite or tungsten; and bonding with a helium leak tight seal the first and second tubes together. The helium leak tight seal maintains its integrity at a temperature of greater than 1100° C.

The present invention pertains to a method for making a mixture for a joint between ceramic tubes or ceramic tubes and metal tubes. The method comprises the steps of putting between 30 wt % (weight percent or percent by mass) and 80 wt % alumina-silicate and between 20 wt % and 70 wt % magnesia-silicate together in powder form to a 100% weight. There is the step of mixing the alumina-silicate and magnesia-silicate together.

The present invention pertains to a method for making a mixture for a joint between metal tubes. The method comprises the steps of putting between 80-10 wt % 80/20 nickel chromium alloy and 20-90 wt % copper of ≥99.99% purity together. There is the step of mixing the nickel chromium alloy and the copper to form an alloy that is then nominally 33 wt % of 80/20 nickel-chromium and 67 wt % copper.

The present invention pertains to a pipe structure for rise at high temperatures, such as in excess of 1100° C., or 1200° C., or 1300° C. or even 1400° C. The structure comprises a first tube of silicon carbide extending in a first direction. The structure comprises a second tube of silicon carbide extending from the first tube, wherein the first and second tubes are bonded with a helium leak tight seal that maintains its integrity at temperatures in excess of 1100° C., or 1200° C., or 1300° C. or even 1400° C.

The subject invention relates to a method for joining bodies of ceramic and/or metals, specifically: silicon carbide, mullite or tungsten to silicon carbide, mullite or tungsten, for use at high temperatures within a pyrolysis furnace for the purpose of ethylene production from feedstock's such as ethane, propane, butanes or naphtha. This pyrolysis furnace may also be used for other high temperature chemical conversation processes, such as propylene or butadiene from similar feedstock as above. Joints are produced using joining materials developed by FM Technologies, Inc. The joints are enhanced by the inclusion of alignment geometry in the bodies to be joined. The joints are enhanced by the constraint of the joining material to the joint region by a capture geometry of the ceramic or metal bodies.

BRIEF DESCRIPTION OF THE SEVERAL VIEWS OF THE DRAWING

In the accompanying drawings, the preferred embodiment of the invention and preferred methods of practicing the invention are illustrated in which:

FIG. 3a is a perspective view of a large diameter to small diameter lap joint.

FIG. 3b is a perspective view of an elbow bend joint.

FIG. 3c is a perspective view of U bend joint.

FIG. 3d is a perspective view of a Y bend joint.

DETAILED DESCRIPTION OF THE INVENTION

Figure 11:
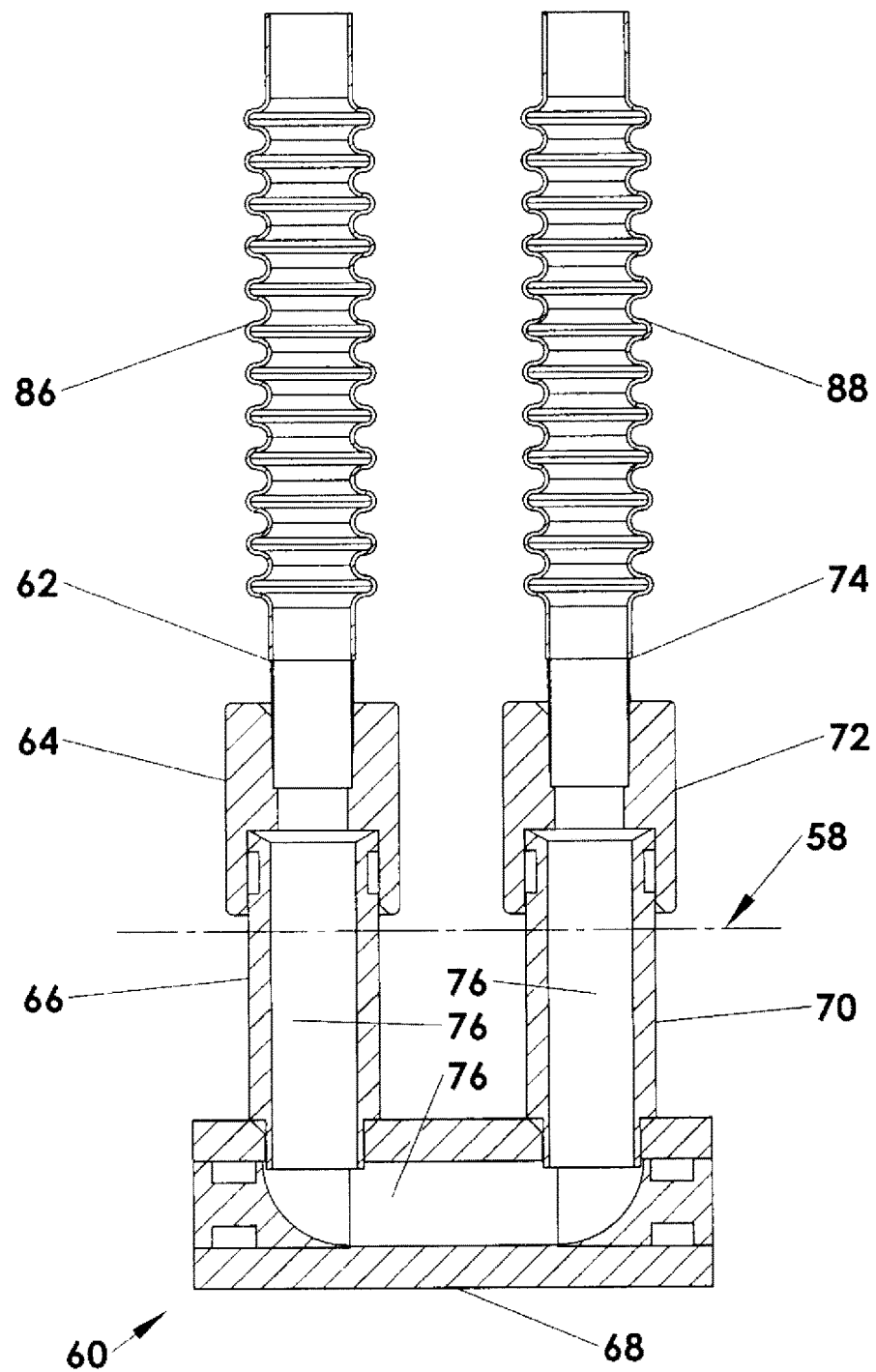
FIG. 11 is a representation of a miniature coil assembly.
Figure 12:
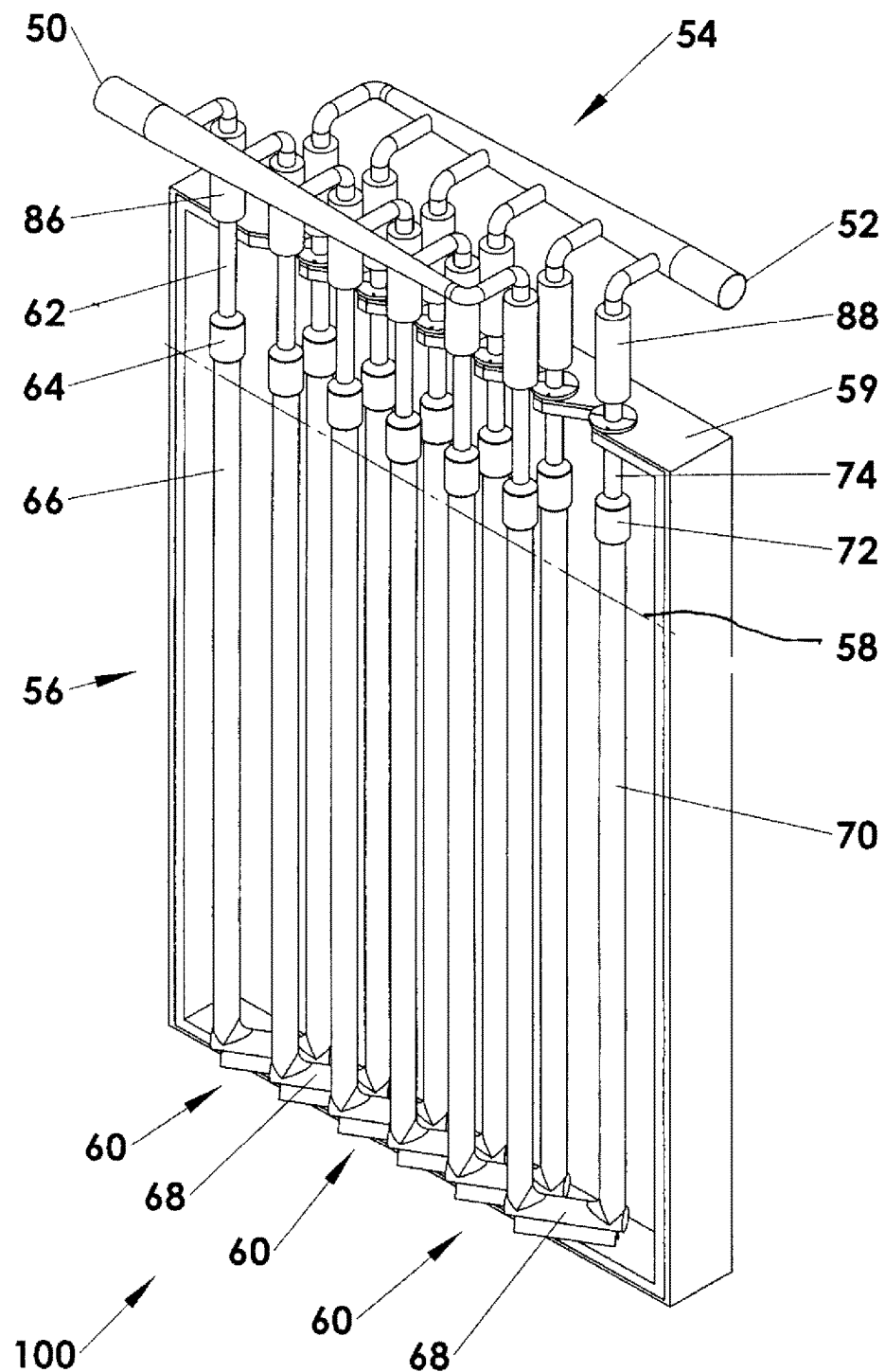
FIG. 12 is a representation of a SiC pyrolysis furnace.

Referring now to the drawings wherein like reference numerals refer to similar or identical parts throughout the several views, and more specifically to FIGS. 11 and 12 thereof, there is shown a system 100 for producing chemicals at high temperature (above 1100 degrees Celsius), such as, ethylene or gasoline. The system 100 comprises a feedstock source 50. The system 100 comprise a chemical conversion portion 54 connected with the feedstock source 50 to receive feedstock and convert the feedstock to ethylene or gasoline. The conversion portion 54 includes a coil array 56 and a furnace 58 that heats the feedstock to temperatures in excess of 1100° C. or 1200° C. or even 1250° C. or even 1300° C. or even 1400° C. The coil array 56 has a plurality of coils 60. Each coil 60 has a right top portion 62 made of super alloy that connects with the source 50 to receive feedstock, a right oxidation protected tungsten coupling 64 that is attached outside the furnace 58 to the right top portion 62 and forms a helium gas tight seal with the right top portion 62, a right bottom portion 66 made of silicon carbide that is attached outside the furnace 58 to the right oxidation protected tungsten coupling 64 and forms a helium gas tight seal with the right oxidation protected tungsten coupling 64, a base 68 made of silicon carbide that is attached to the right bottom portion 66 and forms a helium gas tight seal with the right bottom portion 66, a left bottom portion 70 made of silicon carbide that is attached to the base 68 and forms a helium gas tight seal with the base 68, a left oxidation protected tungsten coupling 72 that is attached to the left bottom portion 70 outside the furnace 58 and forms a helium gas tight seal with the left bottom portion 70, and a left top portion 74 made of super alloy that is attached outside the furnace 58 to the left oxidation protected tungsten coupling 72 and forms a helium gas tight seal with the left oxidation protected tungsten coupling 72. The right top portion 62 and the right oxidation protected tungsten coupling 64 and the right bottom portion 66 and the base 68 and the left bottom portion 70 and the left oxidation protected tungsten coupling 72 and the left top portion 74 being hollow and defining a channel 76 through which feedstock flows and is heated by the furnace 58 to produce ethylene from the feedstock. The furnace 58 heats the left bottom portion 70 and the base 68 and the right bottom portion 66 to temperatures in excess of 1100° C. The system 100 comprises a reservoir 52 connected with the left top portion 74 of each coil 60 to receive ethylene or gasoline from the left top portion 74 of each coil 60.

Figure 13:
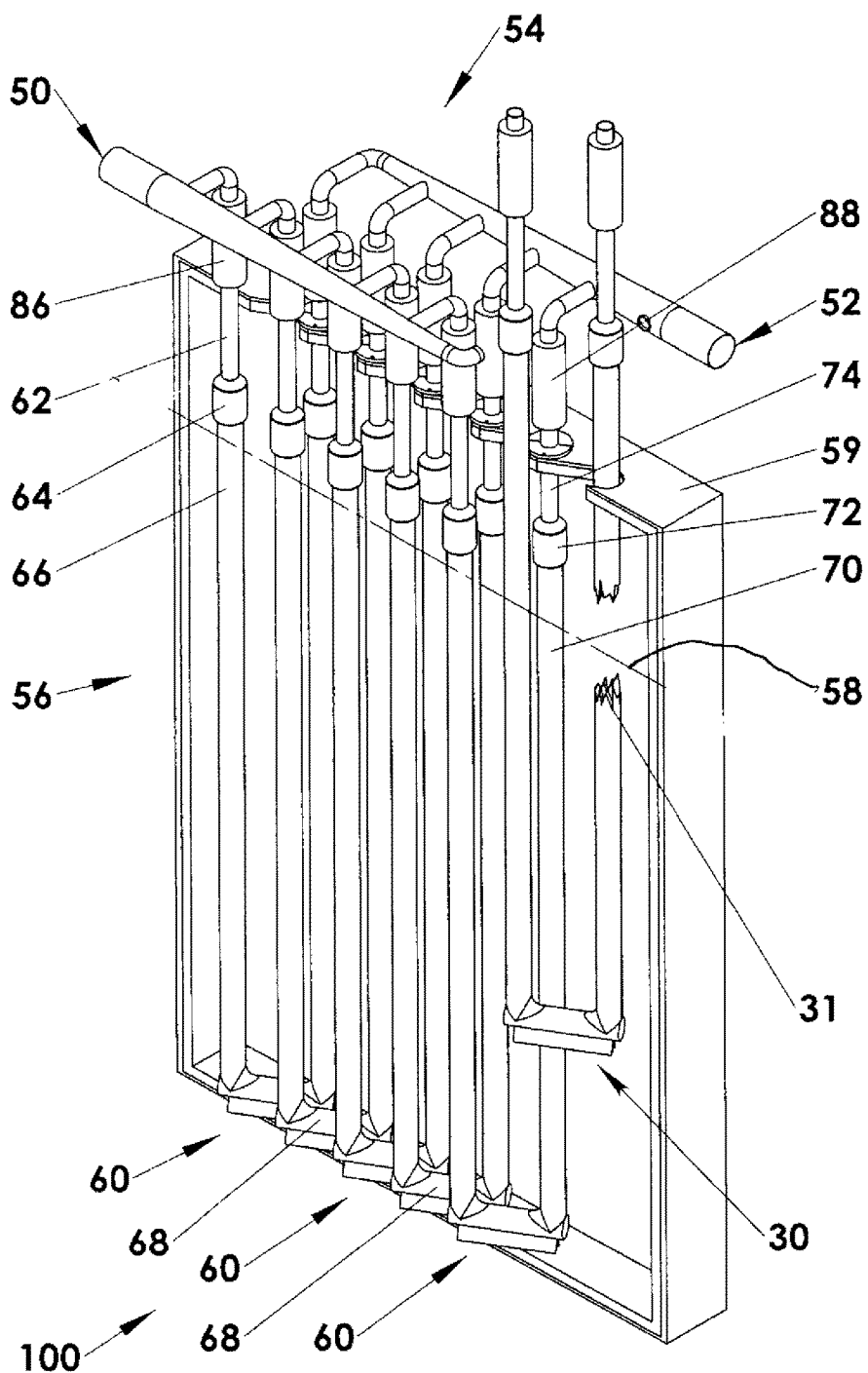
FIG. 13 is a representation of a SiC pyrolysis furnace repair scenario.

The right top portion 62 and the right oxidation protected tungsten coupling 64 and the right bottom portion 66 may be in parallel with the left top portion 74 and the left oxidation protected tungsten coupling 72 and the left the bottom portion 70. The plurality of coils 60 may be in parallel. The system 100 may include a feedstock tube 78 having feedstock branches 80 which extend from the feedstock tube 78 and are attached to right top portions 62 through which feedstock flows to each of the coils 60, and a reservoir tube 82 having reservoir branches 84 which extend from the reservoir tube 82 and is attached to left top portions 74 through which ethylene or gasoline flows to the reservoir 52 from the coils 60. Each coil 60 may include a right bellows 86 part of the right top portion 62, and a left bellows 88 part of the left top portion to accommodate thermal expansion of the coil 60. There may be a housing 59 in which the coil array 56 is disposed and the right and left top portions extend out of to connect to the feedstock tube 78 or the reservoir tube 82 and in which the furnace 58 is disposed. As shown in FIGS. 12 and 13, the furnace 58 is represented by a dashed line across the housing, which represents the top of the furnace 58. The furnace itself in regard to the production of flame and heat to generate the temperatures in excess of 1100° C., or 1200° C., 1300° C. or even 1400° C., is well known in the art.

The present invention pertains to a method for producing ethylene or gasoline. The method comprises the steps of flowing feedstock from a feedstock source to a chemical conversion portion 54 connected with the feedstock source 50 to receive feedstock and convert the feedstock to ethylene or gasoline. The conversion portion 54 includes a coil array 56 and a furnace 58 that heats the feedstock to temperatures in excess of 1100° C. or 1200° C. or even 1250° C. or even 1300° C. or even 1400° C. The coil array 56 has a plurality of coils 60. Each coil 60 has a right top portion 62 made of super alloy that connects with the source 50 to receive feedstock, a right oxidation protected tungsten coupling 64 that is attached outside the furnace 58 to the right top portion 62 and forms a helium gas tight seal with the right top portion 62, a right bottom portion 66 made of silicon carbide that is attached to the right oxidation protected tungsten coupling 64 and forms a helium gas tight seal with the right oxidation protected tungsten coupling 64, a base 68 made of silicon carbide that is attached to the right bottom portion 66 and forms a helium gas tight seal with the right bottom portion 66, a left bottom portion 70 made of silicon carbide that is attached to the base 68 and forms a helium gas tight seal with the base 68, a left oxidation protected tungsten coupling 72 that is attached to the left bottom, portion 70 and forms a helium gas tight seal with the left bottom portion 70, and a left top portion 74 made of super alloy that is attached outside the furnace 58 to the left oxidation protected tungsten coupling 72 and forms a helium gas tight seal with the left oxidation protected tungsten coupling 12. The right top portion 62 and the right oxidation protected tungsten coupling 64 and the right bottom portion 66 and the base 68 and the left bottom portion 70 and the left oxidation protected tungsten coupling 72 and the left top portion 74 being hollow and defining a channel 76 through which feedstock flows and is heated by the furnace 58 to produce ethylene or gasoline from the feedstock. The furnace 58 heats the left bottom portion 70 and the base 68 and the right bottom portion 66 to temperatures in excess of 1100° C. There is the step of receiving ethylene or gasoline at a reservoir 52 from the left top portion 74 of each coil 60. There may be the step of removing a coil 60 from the housing 59 without moving or disturbing any of the other coils 60 in the coil array 56 when the coil 60 needs to be replaced, for instance if the coil 60 becomes damaged.

The present invention pertains to a method for forming an assembly. The method comprises the steps of placing a first tube of silicon carbide or mullite adjacent a second tube of silicon carbide or mullite or tungsten; and bonding with a helium leak tight seal the first and second tubes together. The helium leak tight seal maintains its integrity at a temperature of greater than 1000° C.

The bonding step may include the step of forming a mixed oxide joint or braze joint between the first tube and second tube. The forming step may include the step of applying a mixture of between 30 wt % (weight percent or percent by mass) and 80 wt % alumina-silicate and between 20 wt % and 70 wt % magnesia-silicate in powder form to a 100% weight between the first and second tubes; or a mixture of between 80-10 wt % 80/20 nickel chromium alloy and 20-90 wt % copper of ≥99.99% purity together. There is the step of mixing the nickel chromium alloy and the copper to form an alloy that is then nominally 33 wt % of 80/20 nickel-chromium and 67 wt % copper. The materials which may be used to form the mixture for the joint are more fully described in the provisional applications listed on page 1, and incorporated by reference herein.

The present invention pertains to a method for making a mixture for a joint between ceramic tubes or ceramic tubes and metal tubes. The method comprises the steps of putting between 30 wt % (weight percent or percent by mass) and 80 wt % alumina-silicate and between 20 wt % and 70 wt % magnesia-silicate together in powder form to a 100% weight. There is the step of mixing the alumina-silicate and magnesia-silicate together. The materials which may be used to form the mixture for the joint are more fully described in the provisional applications listed on page 1, and incorporated by reference herein.

The present invention pertains to a method for making a mixture for a joint between metal tubes. The method comprises the steps of putting between 80-10 wt % 80/20 nickel chromium alloy and 20-90 wt % copper of ≥99.99% purity together. There is the step of mixing the nickel chromium alloy and the copper to form an alloy that is then nominally 33 wt % of 80/20 nickel-chromium and 67 wt % copper. The materials which may be used to form the mixture for the joint are more fully described in the provisional applications listed on page 1, and incorporated by reference herein.

The present invention pertains to a pipe structure for use at high temperatures, such as in excess of 1100° C., or 1200° C., or 1300° C. or even 1400° C. The structure comprises a first tube of silicon carbide extending in a first direction. The structure comprises a second tube of silicon carbide extending from the first tube, wherein the first and second tubes are bonded with a helium leak tight seal that maintains its integrity at temperatures in excess of 1100° C., or =1200° C., or 1300° C. or even 1400° C.

In the operation of the invention, the forms of ceramic and metal bodies 10, specifically: silicon carbide, mullite or tungsten bodies 10 capable of being joined by the described method include shapes, such as, plate, rod, ball, tube, and others. These bodies 10 may be joined to either similar or dissimilar silicon carbide, mullite or tungsten shapes. (FIGS. 1-5). A pyrolysis furnace coil fabricated rising the described method may contain as many as 2 different joint types to be described of either mixed oxide joints or braze joints.

Combinations of silicon carbide, mullite or tungsten bodies 10 joined by this technique require only a close fit with a thin layer of joining material, either as a slurry or dry powder 12, between them. A close fit is defined as the opposing surfaces of the two bodies that are being joined having essentially the same shape so their surfaces essentially conform. The opposing surfaces do not have to be exactly the same shape. The joining material will fill any gap that may exist between the opposing surfaces. The joint gap spacing can range from 2 microns to 150 microns, but stronger joints are attained in the range of 10 microns to 50 microns. The assembly is joined by heating the joining material 12 until it reaches a liquid phase for silicon carbide, mullite or tungsten to silicon carbide or mullite. Many tube assembly geometries are possible, including, but not limited to, those of FIGS. 1-10. Additionally, the joining of multiple silicon carbide, mullite and tungsten pieces onto a single silicon carbide, mullite and tungsten piece is considered. This allows, for example, the assembly of a structure consisting of a header with multiple tubes attached as in FIG. 4.

When joining silicon carbide, mullite or tungsten to silicon carbide or mullite, the joining material, applied as either a slurry or dry powder 12, is composed of a mixture of oxides with or without a single or multi-modal silicon carbide powder. The slurry or dry powder covers the surfaces being joined or is provided a path to do so from a reservoir once it has a reached a liquid phase. The multi-modal powder is composed of a mixture of two or more silicon carbide particle sizes. When joining mullite to tungsten for the purpose of transitioning from ceramic furnace material to conventional metal, the joining material, applied as either a slurry of dry powder 12, is composed of a mixture of metals, alloys or oxides. The slurry or dry powder covers the surfaces being joined or is provided a path to do so from a reservoir once it has a reached a liquid phase. When joining tungsten to a superalloy material for the purpose of transitioning back to conventional superalloy metal, the joining material, applied as either a slurry or dry powder 12, is composed of a mixture of metals or alloys that are used to create a braze joint. The joining material 12 is applied thinly between the ceramic/metal bodies 10 to be joined. The powder or slurry 12 is converted to a solid during a heating and cooling cycle and forms a tightly bound transition layer in the joint. The degree to which the joining material 12 in the prepared joint is heated is important to ensure a useful joint. The slurry is prepared by mixing powders with a volatile liquid binder. This allows the slurry to be applied to the parts for joining, and volatility provides the ability to remove the liquid binder before the joining cycle to prevent contamination.

To insure that the ceramic or metal bodies 10 are aligned properly with respect to each other and to the joint, the geometry of the ceramic or metal bodies 10 may be modified by the use of a step, a groove or a taper. These geometric modifications may be in an additional body besides those bodies 10 to be joined, or the geometric modifications may be included in the joining bodies 10.

To provide for the joining material as a slurry or powder 12 to be in good contact with the joint interface, the geometry of the ceramic or metal bodies 10 in or near contact with the joint interface may be modified. For mixed oxide and braze joints, a capture geometry may be devised to (1) constrain the joining material 12 in the region between the ceramic bodies 10 to be joined, and (2) provide a reservoir of joining material 12 which may wick into in the region between the ceramic or metal bodies 10 to be joined when the joining material reaches a temperature at which it can flow into the joint interface through capillary action. The capture geometry and alignment geometries may be combined, and in some cases may be identical. Mixed oxide joints may be achieved anywhere in the range from 1450° C. up to 1650° C. Braze joints may be achieved anywhere in the range from 700° C. up to 1350° C.

Figure 1:
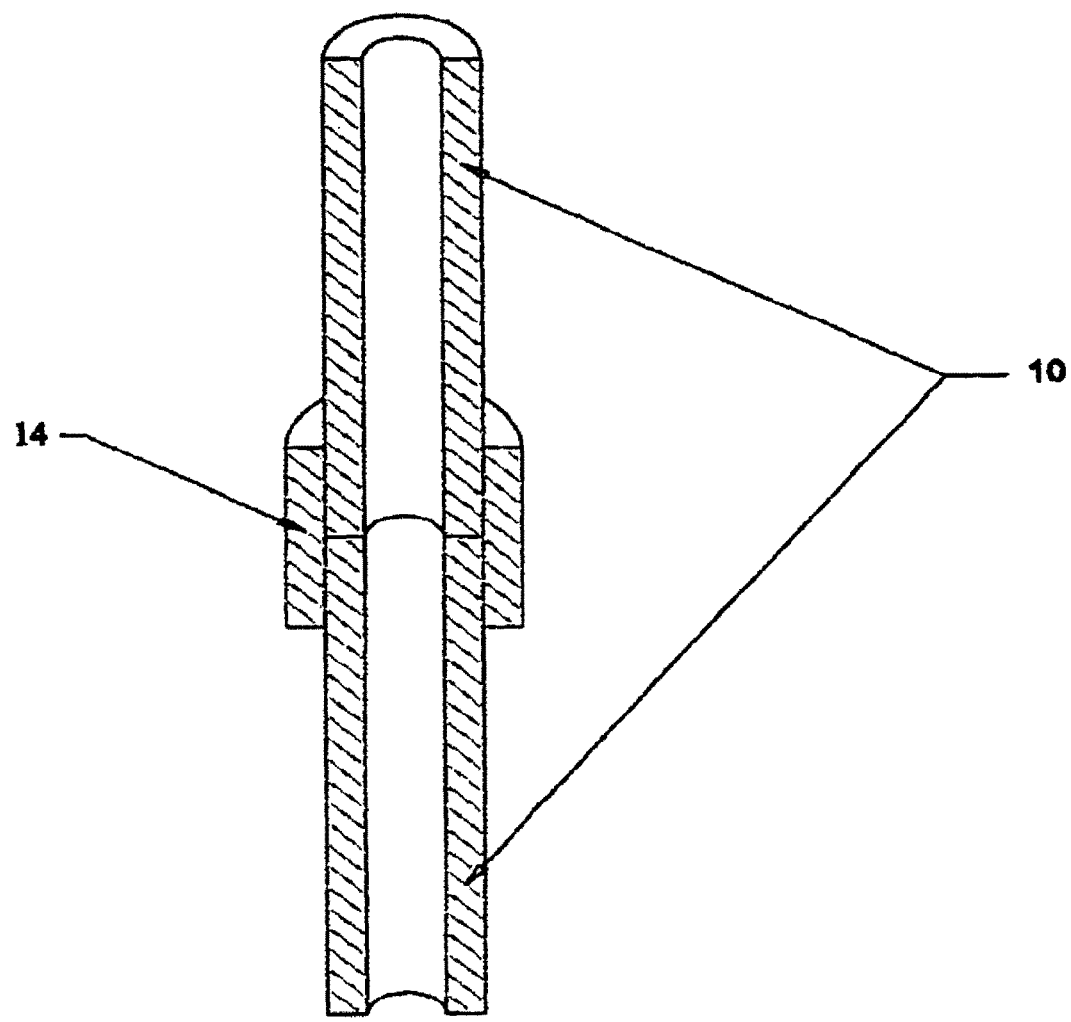
FIG. 1 is a cross-sectional view of a collar around ceramic bodies.
Figure 2:
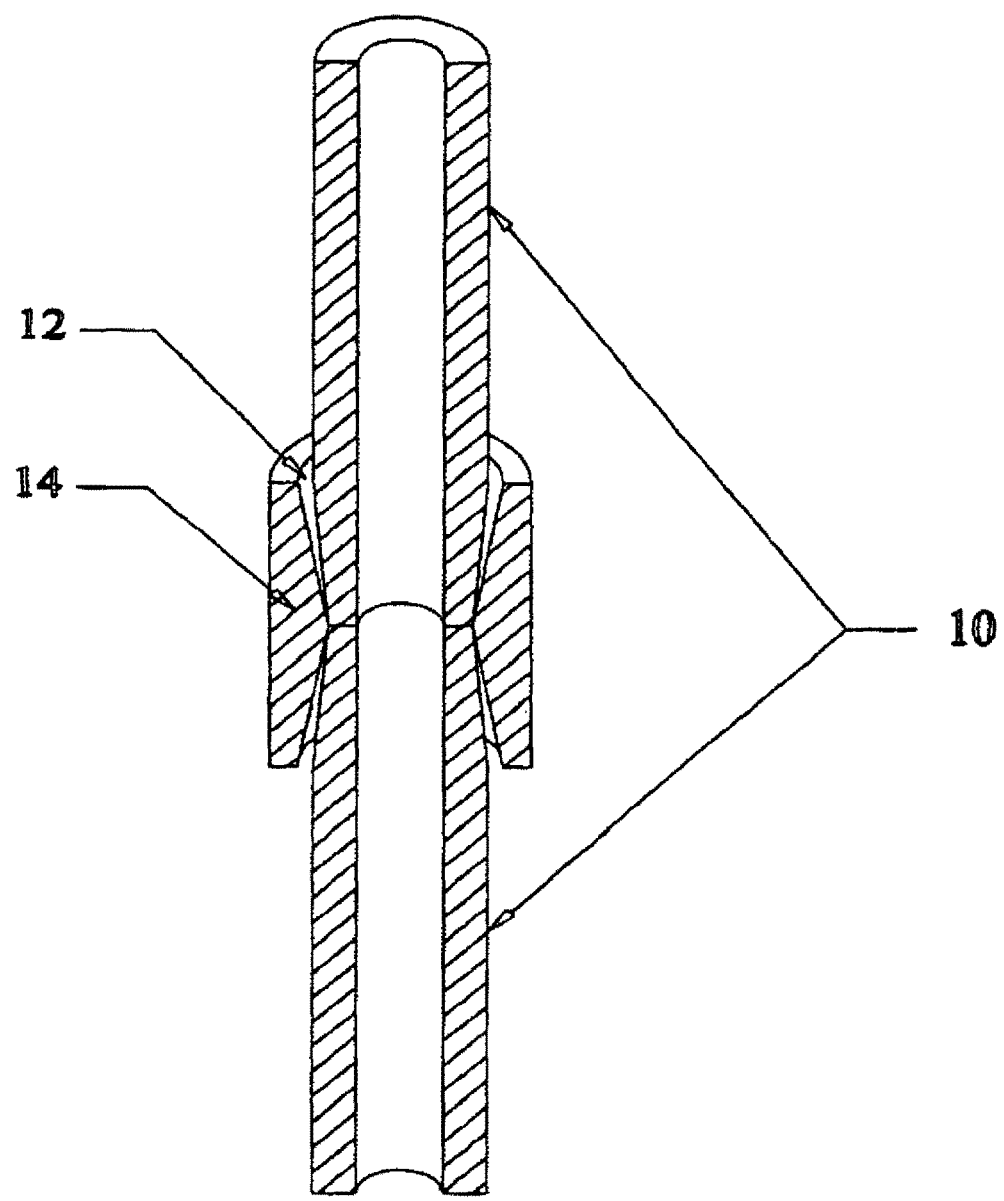
FIG. 2 is a cross-sectional view of a collar with a greater taper angle and ceramic bodies with a lesser taper angle.
Figure 4A:
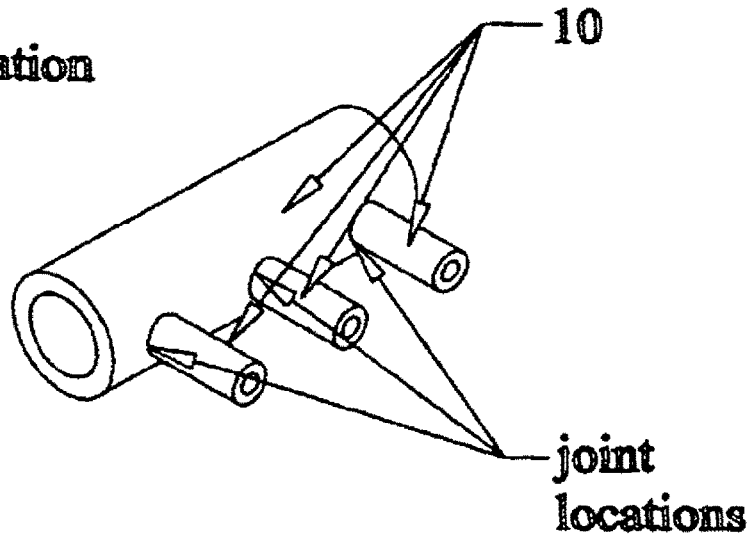
FIG. 4a is a perspective view of a large pipe connected to smaller pipes.
Figure 4B:
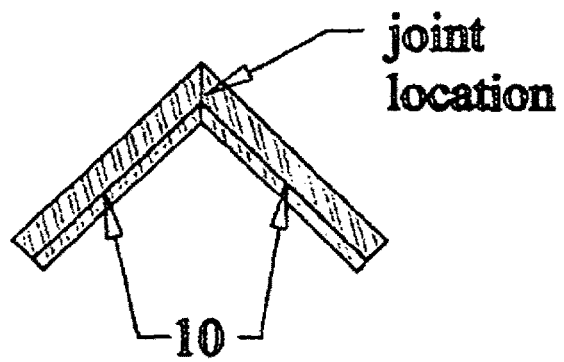
FIG. 4b is a perspective view of a corner.

To make a joint with both an alignment and capture geometry, as shown in FIG. 2, the collar 14 is machined with an inner taper that is 0.5-10 degrees halfway through on both ends of the collar 14 and the tubes 10 are machined with outer tapers that are 0-9.5 degree at the ends that are intended to be joined. The tube 10 tapers are always smaller than the collar tapers. The outer tapers at the tube 10 ends go as deep as one inner taper on the collar 14 that was machined halfway through. When the tube 10 ends are joined to the collar 14, the tapers provide alignment during heating and also a reservoir for bonding slurry 12. Because of the shallower taper angle on the tube ends compared to the collar 14, there is a volume between the tapers that acts as reservoir for the bonding slurry 12.

As mentioned, this technology makes use of up to 2 distinct joint types, mixed oxide joints and braze joints. Mixed oxide joints are used for both ceramic to ceramic and ceramic to metal joints between silicon carbide, mullite or tungsten and silicon carbide, mullite or tungsten. The mixed oxide joints make use of a material known as Makotite™. Makotite™ is a mixed oxide material developed and produced by FM Technologies, Inc. Although other Makotite™ formulations can be used, the formulation best suited for this particular application involves a mixture of between 30 wt % (weight percent or percent by mass) and 80 wt %, nominally 60 wt %, alumina-silicate, also known as Lava or Wonder Stone, and between 20 wt % and 70 wt %, nominally 40 wt %, magnesia-silicate, also known as Steatite. The alumina-silicate and magnesia-silicate are mixed in powder form to a 100% weight fraction to form Makotite™. When mixing powders, any particle size from 150 microns down to nanometer scale particles, or combination thereof, are acceptable for the alumina-silicate and magnesia-silicate constituent materials. The powders can be used as is in this basic mixture, but it is preferable to mill the powder mixture using a planetary ball mill for between 4 and 12 hours. Once prepared, the Makotite™ joining material is applied as a slurry or dry powder that covers the surfaces being joined with a volume of joining material that is greater than or equal to the volume of empty space present between the surfaces to be joined when assembled prior to application of the joining material. If a slurry is the desired form of applications the slurry is created by mixing the prepared Makotite™ powder with a volatile liquid binder such as water or alcohol that is allowed to evaporate as the joint assembly is heated. Once sufficient joining material has been applied in and/or around the joint area, fixturing is applied to hold the coupled parts together prior to heating. The type and level of fixturing is dependent on the size and configuration of parts to be joined. Examples of fixturing used are gravity, if the parts overlap and are able stand in a stable manner once assembled, or graphite sleeves that are shaped to match the parts and removed after joining is complete or, in the case of long parts greater than 0.5 m in length, gripping the parts outside of the heating area using something such as a Wilson seals that act to hold the assembly together. Once parts are assembled and fixed, the joint is heated, either radiantly or using microwaves and in either vacuum or an inert gas atmosphere, to between 1450° C. and 1650° C. to allow the joining material to achieve a liquid phase, and held at temperature for between 1 minute and 5 minutes to allow the joining material to spread evenly within the joint area. The joint is then allowed to cool to room temperature, and is ready to either be joined to other ceramic of metal parts or be used as part of a furnace coil assembly.

Braze joints are used to join tungsten to a superalloy material, such as Inconel-600, for the purpose of transitioning back to conventional metal outside of the ethylene pyrolysis furnace firebox. The preferred joining material, applied as either a slurry or dry powder, is a mixture of 80 wt %-10 wt % 80/20 nickel-chromium alloy powder, also known as Nichrome V, and 20 wt %-90 wt % copper wire or grain of ≥99.99% purity. The best resultant alloy is nominally 33 wt % of 80/20 nickel-chromium and 67 wt % copper. The order of assembly is as follows. First the superalloy tube is interference fit to the tungsten tube to create a seal. Next the copper wire or grain is placed between the superalloy and tungsten tubes in a capture groove or angled joint, such as in FIG. 2. Finally, the nickel-chromium alloy powder is packed on top of the copper wire or grain. This joint is then heated to 800° C. in vacuum, an atmosphere of 99.99% Argon gas is added and the temperature raised to 1200° C. for 1-5 minutes. The assembly is then allowed to cool to room temperature. This arrangement forms a graded layer where most of the copper at the bottom of the groove or taper is alloyed with nickel-chromium. From the bottom of the groove or taper, the concentration of alloy becomes primarily nickel-chromium, in this way forming a helium gas tight joint with ductility and oxidation resistance to over 1000° C. If a lower temperature braze joint is desired, any ductile oxidation resistant braze alloy with a liquidus temperature as low as 700° C. may be used, if the service temperature allows this, in place of the copper-nickel-chromium braze alloy as described above. Higher temperature brazes up to about 1350° C. may be used, but certainly the braze melting temperature must be below the melting temperature of the superalloy unless it is desired to cast the superalloy directly to the tungsten. For the purpose of ethylene production, oxidation protection must be provided to any exposed tungsten material, i.e. tungsten surfaces not coated with oxide joining material, silicon carbide or mullite. Reactive evaporation and/or plating of chromium may be used to apply a first level of high temperature (450° C. to 1000° C.) oxidation protection to the exposed tungsten. Reactive evaporation is preferred as it will provide an overlay of material across the interface of the exposed tungsten and the oxide joining material, silicon carbide or mullite. Plating alone could leave the tungsten, vulnerable at these interfaces. Reactive evaporation, in this case, takes advantage of the relatively high vapor pressure of chromium ranging from $1\times10^{-5}$ torr to 0.1 torr at temperatures between the desired service temperature of the ceramic to metal joint of 900-1000° C. and the temperature of the mixed oxide joining operation of 1450-1650° C. To perform the reactive evaporation, the tungsten part or assembly is immersed in chromium powder or pellets with the assistance of a graphite or boron nitride crucible or form. Once prepared, the powder immersed part or assembly is heated, either radiantly or using microwaves, to between 1100° C. and 1400° C. in vacuum and held at temperature for 10 minutes to 1 hour to allow the chromium powder to evaporatively coat the tungsten part or assembly. Having both the chromium powder and tungsten part or assembly at elevated temperature allows for a more strongly bonded evaporative coating. The joint is then allowed to cool to room temperature. A 20-100 micron thick layer of chromium is formed in 30 minutes at 1250° C., Remaining chromium bulk must be removed before any plating process is performed; this is done by scraping of the excess chromium. Conventional electroplating techniques are then applied to achieve a 25 micron to 150 micron final oxidation resistant coating. Nickel or nickel-chromium alloys, NixCry, may also be applied by reactive evaporation or plating after application of the initial chromium layer to improve oxidation resistance further.

Using this described joining technology, every ceramic to ceramic and ceramic to metal joint is helium leak tight to less than $1\times10^{-9}$ torr.-L./sec. helium leak, rate, and oxidation resistant with service temperature from 1100-1500° C. for ceramic to ceramic and 900-1000° C. for ceramic to metal. The joints have strengths comparable to the as received materials. For ceramic to ceramic joints, flexural strength is 334 MPa and shear strength is 241 MPa. For ceramic to metal joints, shear strength is greater than 308 MPa.

The goal of these joining operations is to create one or more complete furnace coils for ethylene production. A complete mini U-shaped coil assembly can also be manufacture for demonstration purposes (FIG. 11). A mini U-shaped coil assembly, although the vertical SiC legs are very short, demonstrates the overall capability. To delineate its size, the bottom square cross-section of SiC has dimensions of one inch by one inch by four inches long and the superalloy pipe diameter is one-half inch. This mini coil itself serves to demonstrate all of the joining elements ability to interface to superalloy pipe for welding to additional superalloy piping. It has SiC to SiC plug joints, SiC to SiC perpendicular tube joints and SiC to superalloy metal joints. The SiC to SiC plug joints axe necessary because SiC pipe bends and elbows are difficult to manufacture. Elbows and U bends can be approximately fabricated using mainly straight tubes. Bends require the junction of two or more pipes. In this mini coil, a square SiC pipe with both ends open was used as the base, requiring sealing with plug joints. In general, SiC pipe will always have at least one end open. A bellows is used after transitioning to superalloy pipe as an expansion joint to relieve stress that results from differential expansion of the coil assembly. The complete mini coil is helium leak tight, with service temperature from 900-1000° C. outside the firebox and 1100-1400° C. inside the firebox. It is oxidation resistant, coke resistant and structurally strong. Furthermore, a mini coil serves as a model for a twenty to eighty foot long coil assembly with an inside diameter of 1-2 inches.

A full size coil section for ethylene production (FIG. 12) will have a length of between twenty and eighty feet, with an inside pipe diameter of 1 to 2 inches. Bellows are used to diminish the stress at the junction between the vertical and horizontal SiC pipes that would arise from differential expansion of the tube legs if the structure were completely rigid. This stress will appear when there is a temperature difference between the two vertical legs and/or if their thermal expansion coefficients are slightly different. A complete pyrolysis furnace (FIG. 12) will include multiple coils sections in either a parallel or series configuration.

A parallel coil furnace configuration would allow for the easiest field repair scenario. The strategy is to replace a modular section of the complete coil on site (FIG. 13). The complete coil is made up of several double pass U-shaped sections that are connected in parallel (FIG. 12). Each vertical SiC long leg of a U-section is transitioned to superalloy and connected to a bellows before connection to the feed or return piping. The process for U-section replacement will simply involve standard cutting and welding of super alloy. Bellows in each vertical leg eliminate stress between the horizontal and vertical tube junction that makes up the base of the U-shaped section. A broken U-coil section is removed vertically from the firebox and replaced (FIG. 13).

EXAMPLES

Figure 5:
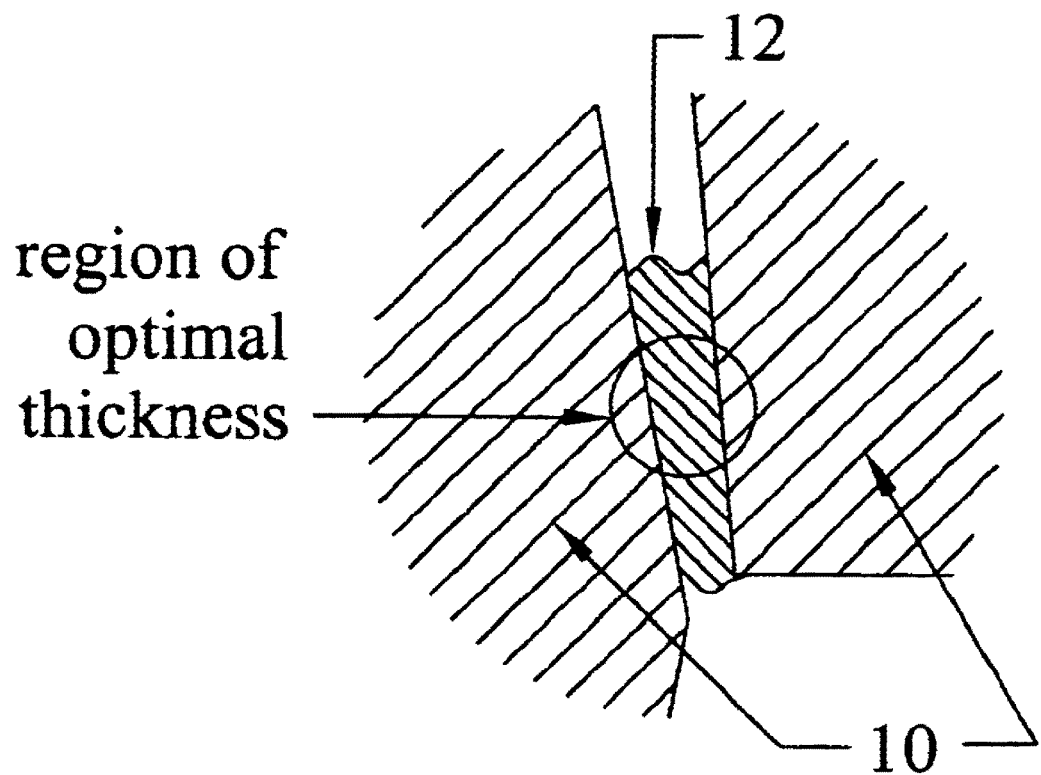
FIG. 5 is a representation of a joint.
Figure 6:
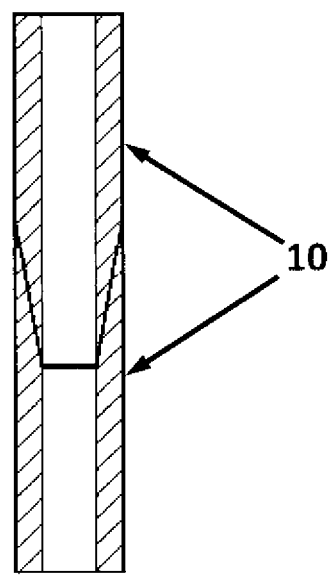
FIG. 6 is a representation of a taper joint.

FIGS. 1-10 display a variety of tube to tube joints. Silicon carbide, mullite or tungsten to silicon carbide, mullite or tungsten butt joints, sleeve joints, step joints, taper joints, groove joints and plug joints have all been made using Makotite™ joining material. All of these joint configurations are helium leak tight. In FIG. 5, the joint was deliberately shown with a wide gap for viewing the joint. Note that the joint gap can be made with nearly zero thickness.

Example 1

Figure 7:
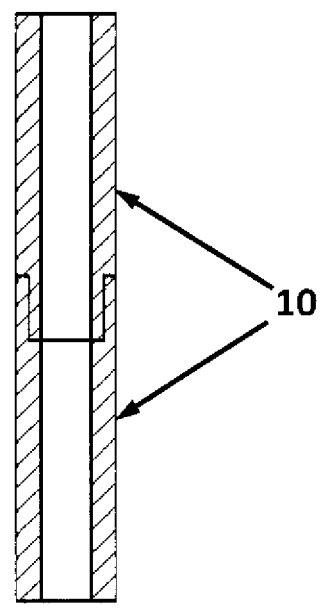
FIG. 7 is a representation of a step joint.
Figure 8:
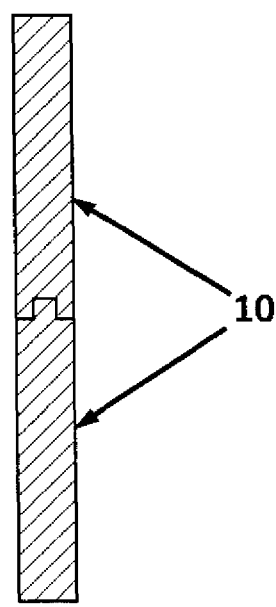
FIG. 8 is a representation of a groove joint.

Two silicon carbide tubes measuring 2.375 in. OD×2 in. ID×6 in. long are machined using diamond based abrasive grinding bits such that one tube has a male step and the other a female step of 0.5 in length, as shown in FIG. 7, with a gap of 0.0015 in between the OD of the male step and the ID of the female step.

Makotite™ joining material is prepared as a slurry by mixing Makotite™ powder with ethanol until a viscosity similar to that of paint is achieved. The slurry is applied between the faces of the steps to be joined 12. Once a layer of slurry of 0.010 in. thickness has been applied in and around the joint area, the female tube is inserted into the male tube and the excess joining material from the radial faces is allowed to collect between the butting faces of the tubes. Graphite fixturing is applied such as to provide a stable base, allowing the assembly to stand vertically as shown in FIG. 7 and a 50 g weight to be placed on top of the assembly to prevent the joint from opening once the joining material has reached a liquid phase upon heating. Once parts are assembled and fixed, the joint assembly is heated radiantly in vacuum to 1200° C. at 5° C. per minute, at which point 1 atmosphere of argon is vented into the furnace. Once in argon, the joint assembly is further heat to 1540° C. at 5° C. per minute to allow the joining material to achieve a liquid phase, and held at temperature for 3 minutes to allow the joining material to spread evenly within the joint area. An atmosphere of argon, or another inert gas, is necessary above 1200° C. to prevent excessive vaporization of SiO2 from the joining material. The joint is then allowed to cool to room temperature at 5° C. per minute, and is ready to either be joined to other ceramic or metal parts or be used as part of a furnace coil assembly.

Example 2

Figure 9:
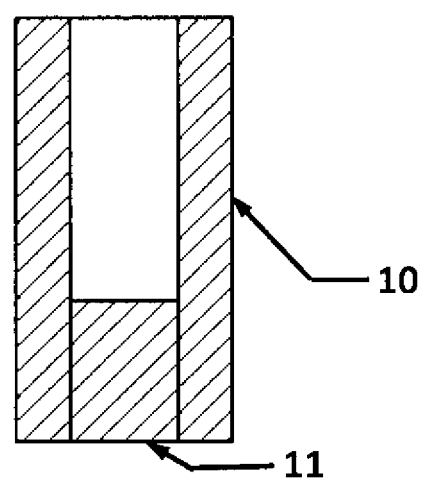
FIG. 9 is a representation of a plug joint.

A 1.25 in. OD×0.946 in. ID×3 in. long tungsten tube and a 1 in. OD×0.5 in. long silicon carbide plug are machined using diamond based abrasive grinding bits such that the tungsten tube has a 3° ID taper at one end that opens to a 1 in. ID at the mouth of the tube and the silicon carbide plug has a 3° OD taper along its entire length that such that one end of the plug retains its original 1 in. OD. When assembled as shown in FIG. 9, this will result in a 0.0016 in. gap for joining material to flow and fill between the OD of the silicon carbide plug and the ID of the tungsten taper.

Makotite™ joining material is prepared as a slurry by mixing Makotite™ powder with ethanol until a viscosity similar to that of paint is achieved. The slurry is applied on the ID of the tapered portion of the tungsten tube and the OD of the silicon plug 12. Once a layer of slurry of 0.010 in thickness has been applied in and around the joint area, the silicon carbide plug is inserted into the tapered end of the tungsten and the excess joining material from the radial faces is allowed to collect on the face of the silicon carbide plug that is inside the tungsten tube. Excess powder from the outward face of the silicon carbide plug is wiped off using an alcohol wipe. The prepared joint assembly is placed on a boron nitride base such that it stands vertically as shown in FIG. 9, allowing the tungsten to act as a weight at the top of the assembly to prevent the joint from opening once the joining material has reached a liquid phase upon heating. Once parts are assembled and fixed, the joint assembly is heated radiantly in vacuum to 1200° C. at 5° C. per minute, at which point 1 atmosphere of argon is vented into the furnace. Once in argon, the joint assembly is further heat to 1540° C. at 5° C. per minute to allow the joining material to achieve a liquid phase, and held at temperature for 3 minutes to allow the joining material to spread evenly within the joint area. An atmosphere of argon, or another inert gas, is necessary above 1200° C. to prevent excessive vaporization of SiO2 from the joining material. The joint is then allowed to cool to room temperature at 5° C. per minute, and is ready to either be joined to other ceramic or metal parts or be used as part of a furnace coil assembly.

Example 3

Figure 10:
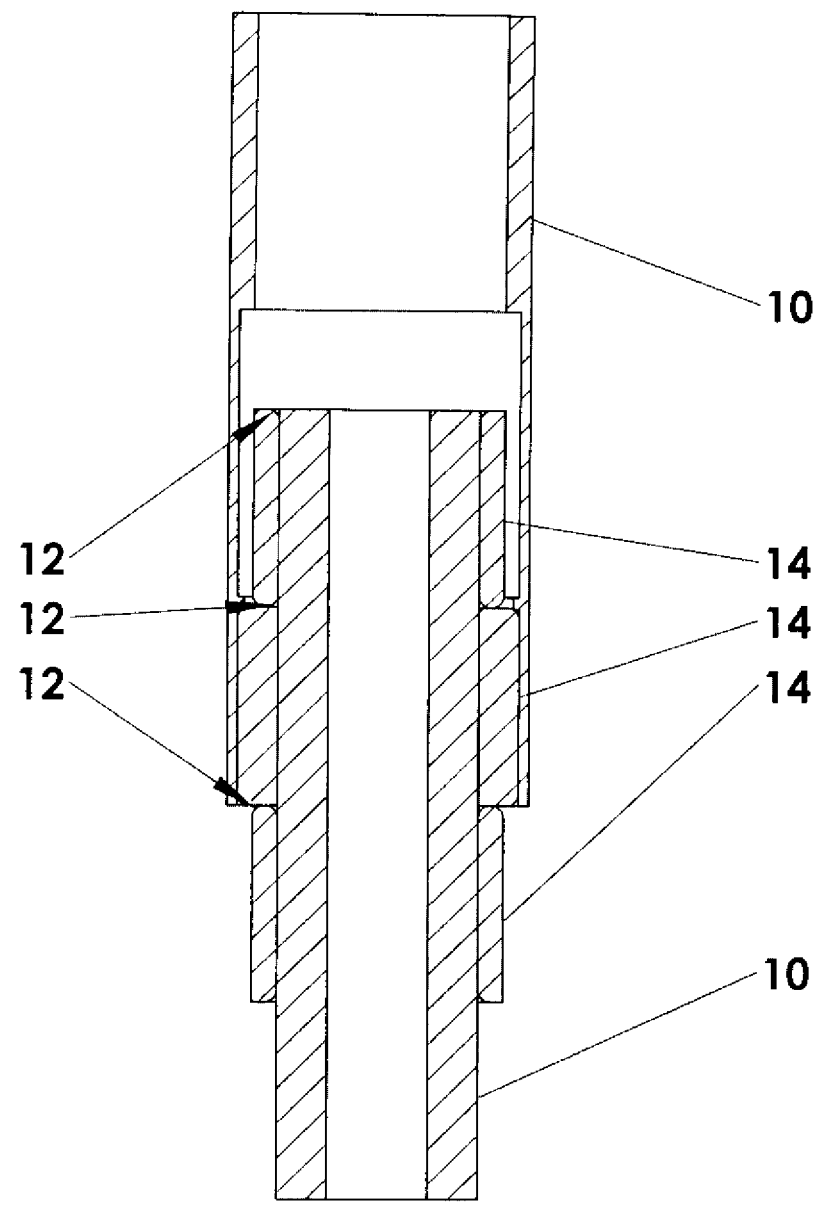
FIG. 10 is a representation of the alternative ceramic to metal joint configuration.

A silicon carbide tube 10 measuring 1.013 in. OD×0.5004 in. ID×6 in. long is machined using diamond grinding bits so that the final OD is 1.000 in. is illustrated in FIG. 10. Three sleeves 14, two are mullite and one is tungsten with the middle sleeve being tungsten, the ID of all three sleeves are diamond ground so as to achieve a final ID of between 1.0015-1.003 in. The sleeves of mullite have an OD of about 1.25 in. and a length of 1 in. The mating mullite and tungsten faces are diamond ground to a flatness of 0.001-0.002 in. The tungsten sleeve 14 has an OD of 1.5 in. and is ground with a 5 degree taper so as to capture the 1.58 in. OD Inconel 600 tube 10 with a mating taper.

Makotite™ joining material is prepared as a slurry by mixing Makotite™ powder with ethanol until a viscosity similar to that of paint is achieved. The slurry is applied between the mating faces of mullite and tungsten 12. The Inconel tube 10 is not being joined yet. Once a layer of slurry of 0.010 in thickness has been applied in and around the joint area, graphite fixturing is applied such as to prevent the mullite sleeves and tungsten sleeve from sliding down from gravity. Once parts are assembled and fixed, the joint assembly is heated radiantly in vacuum to 1200° C. at 5° C. per minute, at which point 1 atmosphere of argon is vented into the furnace. Once in argon, the joint assembly is further heat to 1540° C. at 5° C. per minute to allow the joining material to achieve a liquid phase, and held at temperature for 3 minutes to allow the joining material to spread evenly within the joint area. An atmosphere of argon, or another inert gas, is necessary above 1200° C. to prevent excessive vaporization of SiO2 from the joining material. The joint is then allowed to cool to room temperature at 5° C. per minute. This subassembly is now ready for joining the tungsten circumference to the Inconel tube. As described above the copper-nickel-chromium braze is applied to the top interface between the tungsten and Inconel 600 tube. The heating cycle brazing is also described above. Once the new assembly is cooled down it is ready for oxidation coating of the tungsten. A graphite crucible is built to hold the new assembly but provide a radial and axial air gap of 0.080-0.0120 in. to allow for chromium powder. Chromium is allowed to coat the exposed tungsten, Inconel and mullite. The chroming process is described above. Once the chroming process is complete the electroplating follows. Finally, a complete oxidation resistant, helium gas tight and strong component is achieved for building furnace coils.

REFERENCES, all of which are incorporated by reference herein.

[1] T. J. Clark, M. J. Hanagan, R. W. Cruse, K. Park, V. A. Szalai, S. J. Rohman, R. M. Mininni, U.S. Pat. No. 5,208,069 May 4, 1993 and EP0540084 B1 Sep. 4, 1996.

[2] F. M. Mako, R. Silberglitt, L. K. Len, Pulsed Electron Beam Joining of Materials, (Israel) Pat. No. 118126/2 (Oct. 3, 1994).

[3] E. M. Mako, R. Silberglitt, L. K. Len, Pulsed Electron Beam Joining of Materials, U.S. Pat. No. 5,599,408 (Feb. 4, 1997).

[4] F. M. Mako, R. L. Bruce, Ceramic Joining, U.S. Pat. No. 6,692,597 B2 (Feb. 17, 2004).

[5] F. M. Mako, R. L. Bruce, Ceramic Joining, PRC (China) Pat No. ZL02824111.8 (Jun. 11, 2008).

[6] F. M. Mako, R. L. Bruce, Ceramic Joining, U.S. Pat. No. 8,337,648 B2 (Dec. 25, 2012).

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. A system for producing ethylene or gasoline comprising:
a feedstock source;
a chemical conversion portion connected with the feedstock source to receive feedstock and convert the feedstock to ethylene or gasoline, the conversion portion including a coil array and a furnace that heats the feedstock to temperatures in excess of 1100° C., the coil array having a plurality of coils, each coil having a right top portion made of super alloy that connects with the source to receive feedstock, a right oxidation protected tungsten coupling that is attached outside the furnace to the right top portion and forms a helium gas tight seal with the right top portion, a right bottom portion made of silicon carbide that is attached outside the furnace to the right oxidation protected tungsten coupling and forms a helium gas tight seal with the right oxidation protected tungsten coupling, a base made of silicon carbide that is attached to the right bottom portion and forms a helium gas tight seal with the right bottom portion, a left bottom portion made of silicon carbide that is attached to the base and forms a helium gas tight seal with the base, a left oxidation protected tungsten coupling that is attached outside the furnace to the left bottom portion and forms a helium gas tight seal with the left bottom portion, and a left top portion made of super alloy that is attached to the left oxidation protected tungsten coupling outside the furnace and forms a helium gas tight seal with the left oxidation protected tungsten coupling, the right top portion and the right oxidation protected tungsten coupling and the right bottom portion and the base and the left bottom portion and the left oxidation protected tungsten coupling and the left top portion being hollow and defining a channel through which feedstock flows and is heated by the furnace to produce ethylene from the feedstock, the furnace heating the left bottom portion and the base and the right bottom portion to temperatures in excess of 1100° C.; and
a reservoir connected with the left top portion of each coil to receive ethylene or gasoline from the left top portion of each coil.

2. The system of claim 1 wherein the right top portion and the right oxidation protected tungsten coupling and the right bottom portion are in parallel with the left top portion and the left oxidation protected tungsten coupling and the left the bottom portion.

3. The system of claim 2 wherein the plurality of coils are in parallel.

4. The system of claim 3 including a feedstock tube having feedstock capillaries which extend from the feedstock tube and are attached to right top portions through which feedstock flows to each of the coils, and a reservoir tube having reservoir capillaries which extend from the reservoir tube and is attached to left top portions through which ethylene or gasoline flows to the reservoir from the coils.

5. A method for producing ethylene or gasoline comprising the steps of:
flowing feedstock from a feedstock source to a chemical conversion portion connected with the feedstock source to receive feedstock and convert the feedstock to ethylene or gasoline, the conversion portion including a coil array and a furnace that heats the feedstock to temperatures in excess of 1100° C., the coil array having a plurality of coils, each coil having a right top portion made of super alloy that connects with the source to receive feedstock, a right oxidation protected tungsten coupling that is attached outside the furnace to the right top portion and forms a helium gas tight seal with the right top portion, a right bottom portion made of silicon carbide that is attached outside the furnace to the right oxidation protected tungsten coupling and forms a helium gas tight seal with the right oxidation protected tungsten coupling, a base made of silicon carbide that is attached to the right bottom portion and forms a helium gas tight seal with the right bottom portion, a left bottom portion made of silicon carbide that is attached to the base and forms a helium gas tight seal with the base, a left oxidation protected tungsten coupling that is attached outside the furnace to the left bottom portion and forms a helium gas tight seal with the left bottom portion, and a left top portion made of super alloy that is attached to the left oxidation protected tungsten coupling outside the furnace and forms a helium gas tight seal with the left oxidation protected tungsten coupling, the right top portion and the right oxidation protected tungsten coupling and the right bottom portion and the base and the left bottom portion and the left oxidation protected tungsten coupling and the left top portion being hollow and defining a channel through which feedstock flows and is heated by the furnace to produce ethylene or gasoline from the feedstock, the furnace heating the left bottom portion and the base and the right bottom portion to temperatures in excess of 1100° C.; and receiving ethylene or gasoline at a reservoir from the left top portion of each coil.

6. A pipe structure for use at high temperatures:
a first tube of silicon carbide extending in a first direction; and a second tube of silicon carbide extending from the first tube, wherein the first and second tubes are bonded with a helium leak tight seal.

7. The pipe structure of claim 6 wherein the second tube extends in a second direction substantially perpendicular to the first direction.

8. The pipe structure of claim 6 further comprising a metal buffer tube extending from the first tube, wherein the first tube and the metal buffer tube are bonded with a helium leak tight.

9. The pipe structure of claim 8 further comprising a superalloy tube extending from the metal buffer tube, wherein the superalloy tube and the metal buffer tube are bonded with a helium leak tight seal.

10. The pipe structure of claim 6 further comprising a first plug of silicon carbide inserted into the second tube of silicon carbide, wherein the first plug and the second tube are bonded with a helium leak tight seal.

11. The pipe structure of claim 10 further comprising a second plug of silicon carbide inserted into the second tube of silicon carbide, wherein the second plug and the second tube are bonded with a helium leak tight seal.

12. The pipe structure of claim 6 further comprising a third tube of silicon carbide extending in the first direction, wherein the third tube and the second tube are bonded with a helium leak tight seal.

13. The pipe structure of claim 12 wherein the second tube extends in a second direction substantially perpendicular to the first direction.

14. The pipe structure of claim 12 wherein the second tube has a rectangular perimeter.

* * * * *